(12) United States Patent
Moon et al.

(10) Patent No.: US 7,550,452 B2
(45) Date of Patent: Jun. 23, 2009

(54) CATIONIC LIPIDS AND USE THEREOF

(75) Inventors: Woo-chul Moon, Seoul (KR); Chul-so Moon, Houston, TX (US); Byung-gu Kim, Seoul (KR); Chan-jae Shin, Seoul (KR); Hyeung-jae Kim, Kyungsangnamdo (KR); Young-ho Moon, Kyunggido (KR); Dong-hwan Kim, Kyunggido (KR); Tae-han Um, Seoul (KR); Hwa-su Kim, Seoul (KR); Mi-kyung Song, Seoul (KR); Seok-beom Song, Daejeon (KR)

(73) Assignee: Goodgene, Inc., Seoul (KR)

( * ) Notice: Subject to any disclaimer, the term of this patent is extended or adjusted under 35 U.S.C. 154(b) by 1077 days.

(21) Appl. No.: 10/381,227

(22) PCT Filed: Sep. 21, 2001
(Under 37 CFR 1.47)

(86) PCT No.: PCT/KR01/01588

§ 371 (c)(1),
(2), (4) Date: Aug. 14, 2003

(87) PCT Pub. No.: WO02/24627

PCT Pub. Date: Mar. 28, 2002

(65) Prior Publication Data
US 2004/0185090 A1    Sep. 23, 2004

(30) Foreign Application Priority Data
Sep. 21, 2000    (KR)    .................... 10-2000-0055400

(51) Int. Cl.
*C07J 9/00*    (2006.01)
*A61K 31/56*    (2006.01)

(52) U.S. Cl. ..................................... 514/182
(58) Field of Classification Search ................ 424/450; 552/544
See application file for complete search history.

(56) References Cited

U.S. PATENT DOCUMENTS

| 5,908,635 A | 6/1999 | Thierry |
| 5,994,317 A | 11/1999 | Wheeler |
| 6,056,938 A | 5/2000 | Unger et al. |
| 6,110,490 A | 8/2000 | Thierry |

FOREIGN PATENT DOCUMENTS

WO    WO 93/05162    3/1993

OTHER PUBLICATIONS

The Osgood File( CBS Radio Network, 2004); AFCNEWSOURCE: Fireflies and Cancer; pp. 1-3.*

(Continued)

*Primary Examiner*—Shengjun Wang
*Assistant Examiner*—Timothy E Betton
(74) *Attorney, Agent, or Firm*—Alston & Bird LLP

(57) ABSTRACT

The present invention relates to cationic lipids, methods for preparing some and methods for effectively transporting anionic molecular substances into cell by using said cationic lipids. The present lipids are compatible to gene therapy due to their stability and highly transporting effects.

10 Claims, 3 Drawing Sheets

OTHER PUBLICATIONS

Zhang, Yuanpeng; Lipid particles having asymmetric lipid coating and method of preparing same, 2003, FreshPatents.com,#20060165770, pp. 1-20.*

Ghosh et al., Advanatage of the Ether Linkage between the Positive Charge and the Cholesteryl Skeleton in Cholesterol-Based Amphiphiles as Vectors for Gene Delivery,(2001-2002), Bioconjugate Chem. (2002), 13, 378-384.*

Bhattacharya et al., The effects of cholesterol inclusion on the vesicular membranes of cationic lipids, Department of Organic Chemistry, Indian Institute of Science, Bangalore, 560 012, India, Biochimica et Biophysica Acta, Biomembranes (1996), 1283(1), 21-30 (Abstract Only).*

Bhattacharya et al., Synthesis, Thermotropic Behavior, and Permeability Porperties of Vesicular Mebranes Composed of Cationic Mixed-Cahin Surfactants, Department of Organic Chemistry, Indian Institute of Science, Bangalore, IA, 560012, India Langmuir (1995), 11(12), 4748-57 (Abstract Only).*

Abid et al., Synthesis of polymerizable and non-polymerizable liquid-crystalline vesicle-forming quaternary ammonium derivatives of cholesterol, Dep. Pure and Appl. Chem., Univ. Strathclyde, Glasgow, G1, 1XL, UK, Polymer Communications (1987), 28(1), 16-19 (Abstract Only).*

Yamuna Krishnan Ghosh, Sandhya S. Visweswariah, and Santanu Bhattacharya, Nature of Linkage Between the Cationic Headgroup and Cholesteryl Skeleton Controls Gene Transfection Efficiency, FEBS Letters 473 (2000), Apr. 14, 2000, pp. 341-344.

Santanu Bhattacharya and Yamuna Krishnan-Ghosh, Vesicle Formation from Oligo (oxyethylene)-Bearing Cholesteryl Amphiphiles: Site-Selective Effects of Oxygethylene Units on the Membrane Order and Thickness, Langmuir 2001, vol. 17, Jun. 29, 2000, pp. 2067-2075.

Amanda J. Bradley, Dana V. Devine, Steven M. Answell, Johan Janzen, and Donald E. Brooks, Inhibition of Liposome-Induced Complement Activation by Incorporated Poly(Ethylene Glycol)-Lipids, Archives of Biochemistry and Biophysics, vol. 357, No. 2, Sep. 15, 1998, pp. 185-194.

Elizabeth G. Nabel, Gregory Plautz, and Gary J. Nabel, Site-Specific Gene Expression in Vivo by Direct Gene Transfer into the Arterial Wall, Science, vol. 249, Sep. 14, 1990, pp. 1285-1288.

Philip L. Felgner, Thomas R. Gadek, Marilyn Holm, Richard Roman, Hardy W. Chan, Michael Wenz, Jeffrey P. Northrop, Gordon M. Ringold, and Mark Danielsen, Lipofection: A Highly Efficient, Lipid-Mediated DNA-Transfection Procedure, Proc. Natl. Acad. Sci. USA, vol. 84, Nov. 1987, pp. 7413-7417.

Chen-Yen Wang and Leaf Huang, pH-Sensitive Immunoliposomes Mediate Target-Cell-Specific Delivery and Controlled Expression of a Foreign Gene in Mouse, Proc. Natl. Acad. Sci. USA, vol. 84, Nov. 1987, pp. 7851-7855.

Various Book Reviews, Nature, vol. 338, Mar. 30, 1989, pp. 337-338.

Philip L. Felgner, Particulate Systems and Polymers for In Vitro and In Vivo Delivery of Polynucleotides, Advanced Drug Delivery Reviews, vol. 5, May 5, 1990, pp. 163-187.

* cited by examiner

CATIONIC LIPIDS AND USE THEREOF

TECHNICAL FIELD

This invention relates to novel cationic lipids which can transfer gene or biologically active drug into cells and their use, in particular, methods which can efficiently transfer molecules with negative charge, including DNA, RNA, protein or biologically active drugs, etc. into cells by using cationic lipids.

BACKGROUND ART

A number of gene transfer methods have been developed so far, which include those using viral vectors such as retrovirus or adenovirus, liposomal vectors composed of cationic amphiphilic lipids, DEAE dextran method, gene transfer methods using synthetic polymers or even gene gun.

Viral vectors usually show high gene transfer efficiency, whereas, they have many demerits: It is rather hard to maintain gene expression for desired periods after gene transfer by using viral vectors. Viral vectors may stimulate host immune defense mechanism, induce inflammation and thus may even aggravate disease status especially on repeated administration. It is hard to selectively transfer viral vectors to target cells or target tissues. It takes rather a long time to cultivate and to prepare enough amount of viral vectors. In addition, viral vectors can induce cancer by integration of viral DNA into host chromosomes and may even provoke fatal events upon genetic recombination with latent homologous virus.

Because of the problems associated with viral vectors, non-viral vectors have recently emerged as safe and promising gene transfer tools, which include cationic lipids, synthetic or natural polymers or particles. These non-viral vectors commonly have limited efficiency of transfection (ie. gene transfer). However, recent remarkable advance of synthetic vectors have made them highly promising tools for gene transfer.

Highly valuable information on gene transfer using cationic liposome are listed in the following representative literatures: Hazinski et al, Science, 249, 1285-1288, 1991; Wang and Huang, Proc. Natl. Acad. Sci. (USA), 84, 7851-7855, 1987; Felgner, et al., Proc. Natl. Acad. Sci. USA, 84, 7413-7416, 1987. As compared with viral vectors, liposomal gene vectors have important merits: They can be safely administered into the body via a number of routes, which include direct injection into target tissue, administration via skin, gastrointestinal tract, or airway and they also can be administered systemically by intravenous injection. Nowadays new synthetic vectors are being systematically designed based on their molecular structure and these are entirely different from existing non-viral gene transfer tools which include calcium phosphate precipitaion, or cationic polymer such as DEAE dextran, polylysine and polybrene, or physical gene transfer methodology such as gene gun or electroporation. Novel synthetic vectors hold reasonable promises of highly valuable medicine which are essential for successful gene therapy and are expected to have big market in the future.

The conventional methods of gene therapy included ex vivo gene transfer in which gene was initially transferred into cells in vitro and then these cells transferred by gene were administered into the body. However, this type of ex vivo gene therapy was too much complicated in methodology and costs too much money to be commonly applied in clinical practice. Nowadays the focus of gene therapy is moving from ex vivo gene therapy to in vivo gene therapy. The goal of modern gene therapy is to develop systemic gene therapy method which can transfer gene efficiently and specifically to target cells without significant toxicity. In this regard, some nonviral vectors are focus of interest and research, which include lipid carrier, in particular cationic liposome, molecular conjugates which transfer genes depending on receptor-mediated endocytosis, and synthetic biopolymer vectors.

Cationic lipid molecules make complex particles with negative charged-DNA molecules by forming stable ionic bonding and these liposome-DNA complex enter inside cells by forming fusion with cell membrane or by natural endocytosis process. Felgner first reported on the use of cationic lipids for gene transfer on 1987 (Felgner, et al., Proc. Natl. Acad. Sci. USA, 84, 7413-7416, 1987). He showed that cationic liposome made of N-[1-(2,3-dioleyloxy)propyl]-N,N,N-triethylammonium chloride (DOTMA), an amino lipid, and dioleoylphosphatidyl ethanolamine (DOPE), a lipid with cell membrane fusion-activity was useful for gene transfer, since when a variety of cationic lipid molecules have been developed and used for gene transfer. DOTMA, a cationic lipid with high gene transfer efficiency, has hydrophobic radical which are composed of C18-aliphatic group with double bonds. With regard to structure of DOTMA, the fourth ammonium salts are bound to the opposite site of hydrophobic radicals which are bound by 3-carbon spacer arm and double ether linker bond. DOTMA has high gene transfer efficiency, but carries high cellular toxicity and also requires a number of lengthy synthetic steps. The mixture of DOTMA and DOPE is being commercially sold in the brand name of Lipofectin.

Cationic lipid molecules used for gene transfer are amphipathic compounds and commonly are composed of 3 parts, including cationic head, spacer and hydrophobic tail. Hydrophobic tail part is usually made of fatty acid derivatives such as oleic acid or myristic acid. Cationic ammonium radical acts as an anchor for the contact of the surface of liposome and cell membrane. Glycerol is included as spacer. From 2 to 15 of carbons are hydrophilic. The first, second, third or fourth ammonium radicals with positive charge at neutral pH are included as cationic head.

Novel derivatives of DOTMA have been developed to increase gene transfer efficiency, which include 1,2-dimyrisyloxypropyl-3-dimethylhydroxyethyl ammonium bromide (DMRIE), N-[1-(2,3-dioleyloxy)propyl]-N,N,N-trimethylammonium methyl sulfate (DOTAP) and 2,3-dioleyloxy-N-[2-(sperminecarboxyamide)ethyl]-N,N-dimethyl-1-propane ammonium trifluoroacetate (DOSPA).

In addition, some cationic lipid derivatives of cholesterol have been developed for gene transfer, which include 3β-[N-(N',N'-dimethylaminoethane)carbamoyl]cholesterol(DC-Chol), dimethyl-dioctadecyl ammonium bromide (DDAB), N-(α-trimethylammonio acetyl)-didodecyl-D-glutamate chloride (TMAC) and dioctadecylamidoglycyl-spermine (DOGS). Depending on their structures and number of positive charges, these cationic lipids are classified into 1) those which provide one positive charge by combination of head of lipid and the fourth amine, third amine, or hydroxyethylic fourth amine and 2) those which provide multiple positive charges by combination of lipids with spermine or polylysine.

Another type of cationic lipid used for gene transfer are detergents composed of the fourth ammonium salt, which include single chain detergent such as cetrimethylammonium bromide and double chain detergent such as dimethyldioctadecyl ammonium bromide. These detergents can transfer gene into animal cells. Amino radicals of these amphiphilic detergents are the fourth radical and single chain is united with the first amine radical without spacer arm or linker bond. These amphiphiles show cellular toxicity on administration to mammalian cells.

Another type of amphiphilic molecules tested include 1,2-dioleoyl-3-(4'-trimethylammonio)butanoyl-sn-glycerol (DOBT), cholesteryl(4'-trimethyl-ammonino)butanoate (choTB) and 1,2-dioleoyl-3-succinyl-sn-glycerol choline ester (DOSC) all of which have similar structure to that of DOTMA and but have limited gene transfer efficiency.

Two types of L-5-carboxyspermine, amphiphilic molecules with the first and second ammonium radicals, have been developed and used for gene transfer, which are often called as lipopolyamine and include dioctadecyl-amidoglycylspermine (DOGS) and dipalmitoyl phosphatidyl ethanolamido-spermine (DPPES). These two amphiphilic molecules are particularly useful to transfect primary endocrine cells without significant cellular toxicity.

Lipopolylysine was also reported to be a mediator of gene transfer, the structure of which contains phospholipid(N-glutaryl-phosphatidyl ethanolamine) and polylysine as ammonium radical. Side chain of lysine and head group of phospholipid are spacer arm and hydrophobic group is a double chain united with spacer arm by double ester bonds. Lipopolysine shows high gene transfer efficiency and is devoid of significant cellular toxicity, but shows gene transfer activity only on scraping treatment of target cells, and therefore is inconvenient and of little value in in vivo gene transfer.

Liposome is a microscopic vesicle which has lipid bilayer. The shape and structure of liposome are highly variable from long tube structure to globular shape. The diameter of liposome range from hundreds of Å to several millimeter. The lipid bilayer structure of liposome is composed of hydrophilic layer and concentrated lamellas. The diameter of liposomal vesicle usually range from 20 to 30,000 nm and liquid film layers which are located between lamellas 3 to 10 nm, respectively. Liposome is classified into 3 types depending on their overall size and characteristics of lamellar structure: multilamellar vesicle (MLV), small unilamellar vesicle (SUV) and large unilamellar vesicle (LUV). SUV generally have diameter of from 20 to 50 nm and their structure are composed of single lipid bilayer surrounding central hydrophilic area. Unilamellar vesicle is produced in diameter of from 50 to 600 nm. Unilamellar vesicle is a single compartment vesicle with uniform size, whereas, MLV has a highly variable size with diameter up to 10,000 nm and multicompartmental structure and contains one or more bilayers. Large LUV has diameter of from 600 to 30,000 nm and contain more than 1 bilayer.

The methods of synthesis of liposome are manifold, but generally three types of methods are used, which are as follows. The first is ultrasonic dispersion method in which metal probe is immersed into the suspension of MLV. This method is commonly used to produce SUV. The second is synthetic method of MLV liposome in which lipids are dissolved in appropriate organic solvent and solvent is removed by gas or air, and then remaining thin membrane of dried lipids are mixed with solution and shaked, and finally lipids are dispersed in the form of lipid aggregates or liposome. The third is synthetic method of LUV liposome in which thin membrane of lipids are slowly hydrated by using distilled water or several types of solution. The other method is based on freezing lyophilization by which lipid film is produced. Lipid film is dissolved in volatile solvent, frozen and then solvent is removed again by using lyophilizer. Addition of drug solution to lyophilized lipid produce liposome which is used as pharmaceutical formulation carrying drugs into the body. Various methods of synthesis of liposome are reported in the literatures and patents (Felgner, P. L. and Ringold, G. M., Nature, 337, 387~388, (1989); WO93/05162, U.S. Pat. Nos. 5,994, 317; 6,056,938).

As described above, liposome are basically synthesized from one or more lipid molecules. A variety of lipids including cationic lipids, neutral lipids or anionic lipids are used to synthesize liposome. In particular cationic lipids have most widely been used to synthesize liposome for gene transfer, but they have several problems: Amines which have been used to make many cationic liposome are chemically unstable and have only short shelf life of vesicle. For example, dimethyl dioctadecyl ammonium bromide, a type of amine, lacks appropriate molecular bonding which are necessary for formation of appropriate lipid bilayer structure of liposome.

To manufacture pharmaceutical preparations of liposome, so called encapsulation of biologically active materials by liposome are necessary, which is carried out by mixing of the materials with lipid followed by formation of liposome. The problems common to the above encapsulation process are that less than 50%, usually only less than 20% of biologically active target materials are encapsulated by liposome, thus another process is necessary to remove un-encapsulated materials, and this removal process may induce damage of encapsulating liposome. Therefore, maintenance of stability of liposome is critical in encapsulation process.

Liposome are most commonly used non-viral DNA transfer vehicle, but other methods also have been in use for gene transfer, which include microinjection, protoplast fusion, liposome fusion, calcium phosphate precipitation, electroporation and retrovirus, etc. Each of the methods has its own merits and demerits. In particular, these methods have only limited gene transfer efficiency, but induce significant toxicity and are so complicated in methodology, which precluded their use in large scale clinical trial of biological therapy or gene therapy. For example, calcium phosphate precipitation method has gene transfer efficiency of only 1 cell out of $10^4$ to $10^7$ cells. Microinjection is efficient in gene transfer to a limited number of cells in vitro, but it is impossible to apply to large number of cells or patients. Protoplast fusion have higher gene transfer efficiency than that of calcium phosphate precipitation method, but requires propylene glycol, which induces significant cellular toxicity. Electroporation method has high gene transfer efficiency but requires special apparatus. Retrovirus has pretty good gene transfer efficiency, but may induce viral infection or cancer to the host which precludes their widespread application in human patients. Liposome have been commonly used for gene transfer, but most of the old style liposome have only limited gene transfer efficiency not so much higher than that of calcium phosphate precipitation method. The ideal method of gene transfer must have high gene transfer efficiency, no cellular toxicity and be free from contamination by infective material and should be simple in methodology so that it does not require complicated apparatus or expensive machine.

DISCLOSURE OF INVENTION

Inventors have carried out diverse experiments to solve the problems of existing gene transfer methods as described above and have found novel cationic lipids which have high gene transfer efficiency, are devoid of significant cellular toxicity or risk of contamination by infective materials and do not require complicated apparatus for application to gene transfer. The present invention is based on these findings.

The purpose of this invention is to provide cationic lipids which can efficiently transfer anionic materials into the cells, including DNA, RNA, protein, peptide or biologically active drugs.

The other purpose of this invention is to provide practical methods which efficiently transfer DNA, RNA, protein, peptide or biologically active drugs into the cells by using the cationic lipids. The cationic lipid made by inventors to accomplish the above purpose has following chemical structure 1:

[Chemical structure 1]

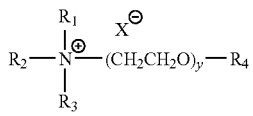

wherein Y is natural number between 1 and 20; each of $R_1$~$R_3$ has same or different hydrogen, alkyl or hydroxyalkyl radical between 1~10 of carbon number, or aryl or aralkyl radical between 7~11 of carbon number; $R_4$ is cholesterol radical; X is any anion which is pharmacologically allowable.

The gene transfer methods using novel cationic lipids described in the invention include (a) the step of formation of lipid complex by contacting effective amounts of cationic lipids and anionic molecules; and (b) the step of contact of the lipid complex and cells.

Lane 1 indicates 1 kb size marker;

Lane 2 indicates migration of naked pCMV-p53 plasmid DNA which is free of contamination by RNA or naked or chromosomal DNA of E. coli;

Lane 3 indicates complex of pCMV-p53 plasmid DNA and liposome which was composed of cationic lipid made in the invention and DOPE lipid (1:1 molar ratio);

Lane 4 indicates complex of pCMV-p53 plasmid DNA and liposome which was composed of cationic lipid made in the invention and DOPE lipid (1:2 molar ratio);

Lane 5 indicates complex of pCMV-p53 plasmid DNA and liposome which was composed of cationic lipid made in this invention and DOPE lipid (1:4 molar ratio), in which this lane shows no mobilization of DNA on electrophoresis and thus indicates complete binding of plasmid DNA and liposome at 1:4 molar ratio;

Lane 6 shows no mobilization of DNA on electrophoresis and thus indicates complete binding of pCMV-p53 plasmid DNA with liposome which was composed of cationic lipid in this invention and DOPE lipid at 1:6 molar ratio; and Lane 7 indicates complex of pCMV-p53 and liposome composed of cationic lipid in this invention and DOPE and PLL (poly-L-lysine) in weight ratio of 1:3:0.375.

Figure 3:
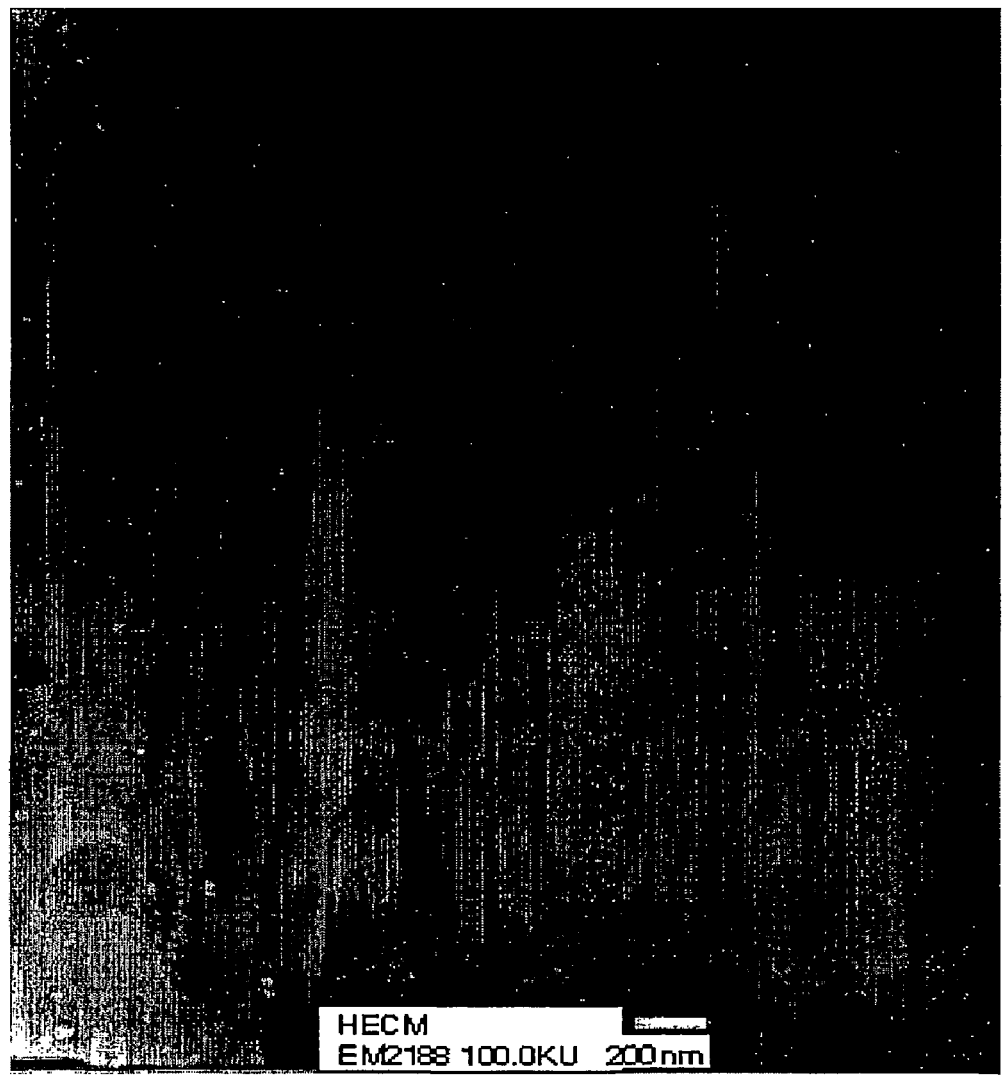

FIG. 3 illustrates scanning electron microscopic finding of liposome composed of cationic lipid made in this invention and DOPE in 1:1 molar ratio.

BEST MODE FOR CARRYING OUT THE INVENTION

The method of this invention is more precisely described in the followings:

As described above, the novel cationic lipids described in this invention is represented by chemical structure 1.

Chemical structure 1

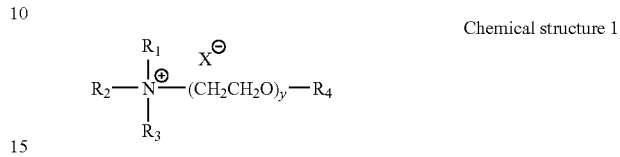

wherein Y is natural number between 1 and 20; each of $R_1$~$R_3$ has same or different hydrogen, alkyl or hydroxyalkyl radical between 1~10 of carbon number, or aryl or aralkyl radical between 7~11 of carbon number; $R_4$ is cholesterol radical; X is any anion which is pharmacologically allowable. It is preferable that Y is natural number between 1 and 12; $R_1$~$R_3$ has one or more hydrogen, alkyl or hydroxyalkyl radical between 2~5 of carbon number; and X is Br, Cl, I, $CH_3CO_2$ or $CF_3CO_2$.

The novel cationic lipids with chemical structure 1 are highly efficient non-viral gene transfer vehicles of mammalian cells. These cationic lipids form complex with anionic molecules such as DNA by stable ionic binding and thus can transfer anionic molecules inside the cells by fusion mechanism of liposome and cell membrane or by natural endocytosis mechanism (Felgner P. L. Adv. Drug Delivery Review, 5, 163(1990)). Cationic portion of lipids form bonds with anionic portion of DNA and coat the chains of DNA, and then lipids become externally located and spontaneously self-conglomerate by hydrophobic bonding and these make DNA molecules into dense particles. These DNA-lipid particles have overall positive charge and usually have diameter of hundreds of nm. These cationic lipid/DNA particles interact in a nonspecific manner with mammalian cell membranes which naturally have negative charge, destabilizes the structure of cell membrane, and then the particles enter inside cells into the cytoplasm. After entering cytoplasm, the DNA/liposome particles are fused with endosome and transferred to lysosome to be destroyed, but some particles escape from lysosome to cytoplasm and then enter nucleus and induce expression of transgene.

The above-mentioned cationic lipids invented by the inventors can form complex with one or more other lipids. Contact of compounds which contain the cationic lipids with anionic molecules make complex, which can deliver anionic molecules. Contact of complex of lipid-anionic molecules with cells make it possible to transfer anionic molecules inside cells.

Cationic lipids in this invention are combined with a number of neutral lipids or so called helper lipids to make liposome, which include dioleylphosphatidyl ethanolamine (DOPE), dioleylphosphatidyl choline (DOPC), phosphatidyl choline (PC), and one or more lipids derived from mPEG-cholesterol or cholesterol. For example, liposome made of mPEG-cholesterol as in EXAMPLE 8 of this invention are characteristically resistant to destruction in in vivo by reticuloendothelial system (RES) or protein and thus can remain inside body and show activity for longer time. The cationic lipids and cationic liposome in this invention work very well in many cells including HeLaS3, HepG2, Hep3B, NIH3T3 and COS7(ATCC, USA). However, these cells are just examples and the efficacy of our novel cationic lipids are not limited to these cells.

Cationic lipids in this invention are made into cationic liposome as in EXAMPLE 8. Cationic liposome are mixed with DNA or drugs to make complex of pharmaceutical preparation as in EXAMPLE 10. These complex of cationic liposome-DNA or cationic liposome-drugs can be applied in vitro to cells under culture or even can be administered in vivo by local injection into target tissue or systemically by intravenous injection and show high gene transfer efficacy.

The cationic lipids in this invention are remarkable for their low cost of production, production in high quality and high yield, and high efficiency of transfer of DNA, RNA, protein, peptide, drugs into the target cells.

The invention is described in more detail in the following examples, but category of this invention is not limited to the following examples.

EXAMPLE 1

A. Synthesis of Cholesteryl Mesylate

The mixture of 200 g (0.52 mol) of cholesterol in 600 ml of anhydrous pyridin was stirred at 0° C. in 1000 mL 4-round bottom flask equipped with mechanical stirrer, thermometer and cooler. Then 114.5 g (1 mol) of methanesulfonyl chloride was slowly added dropwise for 30 min, and the mixture was stirred for 10 hrs at 0° C. The reaction mixture was dissolved in 1,000 ml of ether, and was washed several times with mixture of distilled water and concentrated HCl (600:400 ml) cooled at 0~5° C. with care to prevent exothermic reaction. The pH of the mixture was adjusted to pH 7 by washing many times with distilled water. Ether layer was dried over anhydrous magnesium sulfate for 3 hours and the solvent was removed on a rotary evaporator. The crude product was purified by acetonitrile recrystallization to give 210 g of white needle crystal (87.4%, mp 95° C.). In case that the reaction mixture is dissolved in methylene chloride instead of ether, contaminated spot appears on TLC and the purification is not enough. This remains even after acetonitrile recrystallization.

$^1$H NMR(CDCl3, ppm): 5.3(t, 1H, C of cholesterol=C$\underline{H}$)
4.42-4.62(m, 1H, CH$_3$SO$_3$C$\underline{H}$)
3.0(s, 3H, C$\underline{H}_3$SO$_3$—)

B. Synthesis of Cholesteryl Triethyleneglycol

The mixture, which is 30 g (64.6 mmol) of cholesteryl mesylate and 210 g (1.4 mol) of purified triethyleneglycol in 600 ml of anhydrous acetonitrile, and 50 ml of 1,4-dioxane, was stirred at 45~55° C. in 1000 mL round bottom flask for 24 hours. The termination of the reaction was confirmed by TLC. The reaction mixture was dissolved in diethyl ether, washed with 1,000 ml of 5% sodium carbonate solution, and then was washed several times with distilled water. The ether layer was dried over anhydrous magnesium sulfate and the solvent was removed on a rotary evaporator. In order to remove the unreacted triethylene glycol and a few elimination product, the crude product was purified by silica gel column by using ether:methanol (9.5:0.5) solvent to give 27 g of product (80.6%)

$^1$H NMR(CDCl3, ppm): 5.3(t, 1H, C of cholesterol=C$\underline{H}$)
3.6-3.8(m, 12H, TEG)
3.0-3.2(m, 1H, HO(CH$_2$CH$_2$O)$_3$C$\underline{H}$—)

C. Synthesis of Cholesteryl Triethyleneglycol Mesylate

Cholesteryl triethyleneglycol mesylate was prepared by using the similar procedures as was used in the synthesis of cholesteryl mesylate. TLC analysis by ether or ether:methanol (9.75:0.25) showed single spot and the crude product was purified by silica gel column chromatography to give 26.7 g of pale viscous solid product (86%).

$^1$H NMR(CDCl3, ppm): 5.3(t, 1H, C of cholesterol=C$\underline{H}$)
4.3(M, 2H, CH$_3$SO$_3$C$\underline{H}_2$CH$_2$O—)
3.5-3.8(m, 10H, CH$_3$SO$_3$CH$_2$C$\underline{H}_2$(OC$\underline{H}_2$C$\underline{H}_2$)$_2$—)
3.0(s, 3H, C$\underline{H}_3$SO$_3$—)

D. Synthesis of Dimethylaminotetraethoxycholesterol

The mixture of 5.2 g (58 mmol) of dimethylethanolamine and 6.53 g (58 mmol) of purified potassium butoxide in 300 ml of anhydrous toluene dried by calcuium hydride and anhydrous potassium carbonate was stirred at 30° C. in nitrogen gas for 1 hr. After the toluene was completely removed on a vacuum pump, 26.7 g (45.5 mmol) of cholesteryl triethyleneglycolmesylate was dissolved in 400 ml of anhydrous acetonitrile and a small volume of anhydrous toluene, and this was mixed in the cooled reactor. The reaction mixture was immediately turned to pale brown yellow, and then the mixture was stirred at room temperature for 18 hours. After solvent was removed on a rotary evaporator, the reaction mixture was dissolved with 1,000 ml of ether and was washed with 500 ml of 10% sodium carbonate. The pH of the mixture was adjusted to 7 by washing several times with 1,000 ml of distilled water. After ether layer was dried over anhydrous magnesium sulfate, the solvent was removed on a rotary evaporator. The concentrated product was purified by silica gel column using Ether:Methanol (495 ml:5 ml) and Ether:Methanol (400 ml:100 ml) solvent continuously. The product was vacuum dried in oil bath at 60° C. for 5 hours and purified to give 14 g of pale high viscous brown product (53%).

$^1$H NMR(CDCl3, ppm): 5.3(t, 1H, C of cholesterol=C$\underline{H}$)
3.0-3.2(m, 1H, —(CH$_2$CH$_2$O)$_3$—C$\underline{H}$—)
2.2(s, 6H, (CH$_3$)$_2$N—)

E. Synthesis of N-(Tetraethoxycholesteryl)-N,N,N-trimethyl ammonium Chloride 11 g (18.6 mmol) of 3-(N,N-Dimethylaminotetraethoxy) cholesterol prepared by using the above-mentioned method was dissolved in 5 ml of anhydrous acetonitrile and put into high pressure reactor. After the reactor was cooled in dry ice, 50 ml of chloromethane was added and the reactor was tightly sealed and was refluxed in oil bath at 70° C. for 48 hours. The product was purified by recrystallization by using anhydrous acetonitrile to give 9.4 g of product (78%).

$^1$H NMR(CDCl3, ppm): 5.3(t, 1H, C=C$\underline{H}$ of cholesterol)
3.9(s, 2H, (CH$_3$)$_3$NC$\underline{H}_2$—)
3.6(s, 9H, (C$\underline{H}_3$)$_3$N—)

The above reaction processes are illustrated in the following reaction scheme 1.

[REACTION 1]

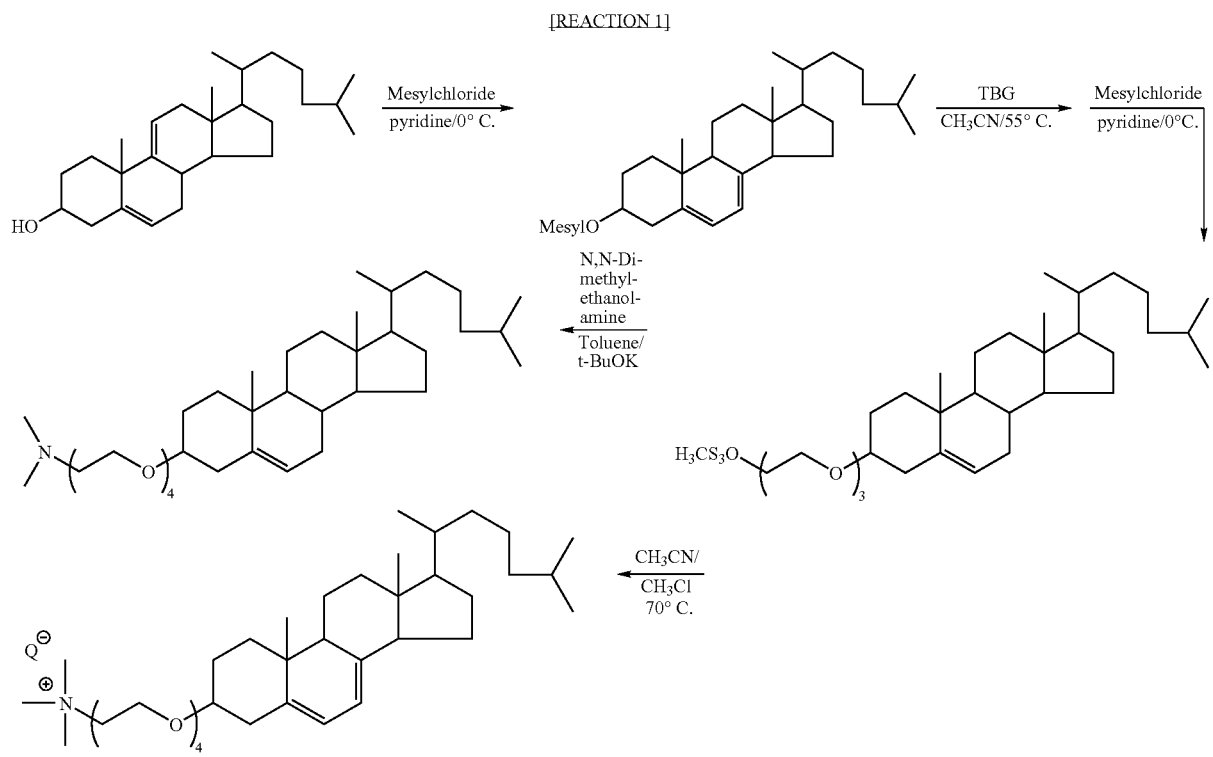

EXAMPLE 2

A. Synthesis of 2-Bromoethoxycholesterol

The mixture of 31 g (66.7 mmol) of cholesteryl mesylate and 14.2 ml (198 mol) of 2-bromoethanol, which was slowly added to 200 ml of anhydrous acetonitrile and was stirred for 24 hours at 60° C.

After the solvent was removed on a rotary evaporator, the reaction mixture was dissolved in 500 ml of distilled water, and then the product was extracted with 1500 ml of diethyl ether. The organic solvent layer was washed several times with distilled water and dried over anhydrous magnesium sulfate, and then the solvent was removed on a rotary evaporator. The crude product was purified on silica gel column by using hexane:ethylacetate (20:1) to give 18 g of white crystal (54.7%).

$^1$H NMR(CDCl3, ppm): 5.3(t, 1H, C of cholesterol=C$\underline{H}$)
3.8(t, 2H, BrC$\underline{H}_2$CH$_2$—O—)
3.5(t, 2H, BrCH$_2$C$\underline{H}_2$O—)
3.1(m, 1H, BrCH$_2$CH$_2$OC$\underline{H}$—)

B. Synthesis of N-Cholesteryloxyethyl-N,N-dimethyl-N-hydroxyethyl ammonium bromide A mixture of 36.6 g (74.1 mmol) of 3-(2-Bromoethyl) cholesterol and 37.3 ml (370 mmol) of N,N-dimethyl ethanolamine which was added in 300 ml of anhydrous acetone and was stirred for 48 hours at 50° C. After the product was filtered and dried on vacuum pump, the crude product was isolated by silica gel column using chloroform:methanol (6:1) and again purified by recrystallization method using ethanol to give 31.1 g of white crystal (72%).

$^1$H NMR(CDCl3, ppm): 5.3(t, 1H, C of cholesterol=C$\underline{H}$)
5.0(s, 1H, $\underline{H}$OCH$_2$CH$_2$N(CH$_3$)$_2$—)
3.4(s, 6H, HOCH$_2$CH$_2$N(C$\underline{H}_3$)$_2$—)

The above reaction processes are illustrated in the following reaction scheme 2.

[REACTION 2]

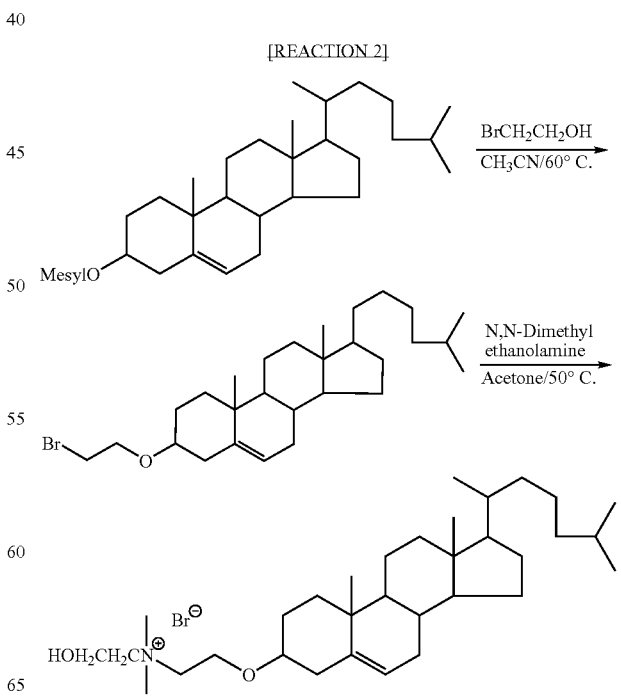

EXAMPLE 3

Synthesis of N-[3-(Cholesteryl)oxyethyl]-N,N-dimethyl-N-[2-(hydroxy)propyl]ammonium bromide A mixture of 6 g (0.01 mol) of 3-(2-Bromoethyl)cholesterol and 47.9 g (44 eq) of N,N-dimethyl-amino-2-propanol was added in 200 ml of anhydrous acetone, and the mixture was stirred for 48 hours at 35~40° C. During reaction white solid material was formed in acetone solvent and the termination of reaction was confirmed by TLC (hexane:ether=4:1). After the mixture was distilled by 150 ml of acetone on a rotary evaporator, the mixture was filtrated by glass filter the white product was filtered and dried at 40t on vacuum pump for 2 hours. The product was re-crystallizated by 200 ml of acetonitrile and 8 ml of anhydrous ethanol. The product was purified by silica gel column using chloroform:methanol (7:3) and then by re-crystallization method using anhydrous ethanol to give 2.5 g of white crystal (42%).

$^1$H NMR(CDCl3, ppm): 5.3(t, 1H, C of cholesterol=C$\underline{H}$)
3.8(m, 1H, CH$_3$(OH)CHCH$_2$—)
3.4(s, 6H, CH$_3$(OH)CHCH$_2$N(CH$_3$)$_2$—)
1.1(d, 3H, CH$_3$(OH)CHCH$_2$—)

The reaction process of EXAMPLE 3 is illustrated in the following reaction scheme 3.

[REACTION 3]

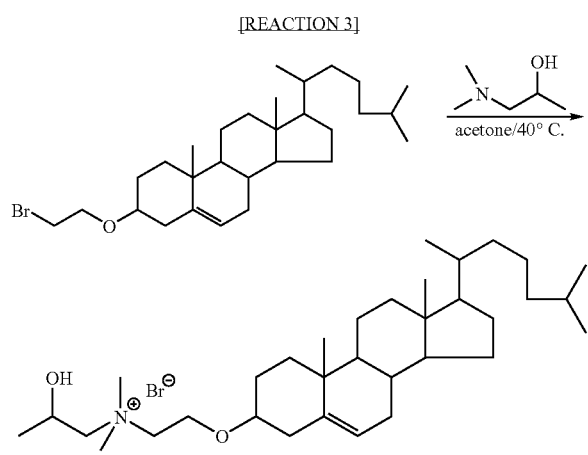

EXAMPLE 4

Synthesis of N-2-[3-(Cholesteryloxy)ethyl]-N,N,N-triethyl ammonium Bromide 50 ml of purified triethyl amine was added in the reactor which contained 5 g (0.01 mol) of 3-(2-bromoethyl)cholesterol and 250 ml of anhydrous acetone and the mixture was stirred for 48 hours at 35~40° C. During reaction white solid was formed in acetone solvent and the termination of reaction was confirmed by TLC. The product was purified by silica gel column using chloroform:methanol (7:3) and by re-crystallization method using anhydrous ethanol to give 2.1 g of moisture-sensitive white crystal (35.6%).

$^1$H NMR(CDCl$_3$, ppm): 5.3(t, 1H, C of cholesterol=C$\underline{H}$)
3.5(m, 8H, (CH$_3$C$\underline{H}_2$)$_3$NC$\underline{H}_2$—)
1.3(t, 9H, (CH$_3$CH$_2$)$_3$N—)

The reaction process of example 4 is illustrated in the following reaction scheme 4.

[REACTION 4]

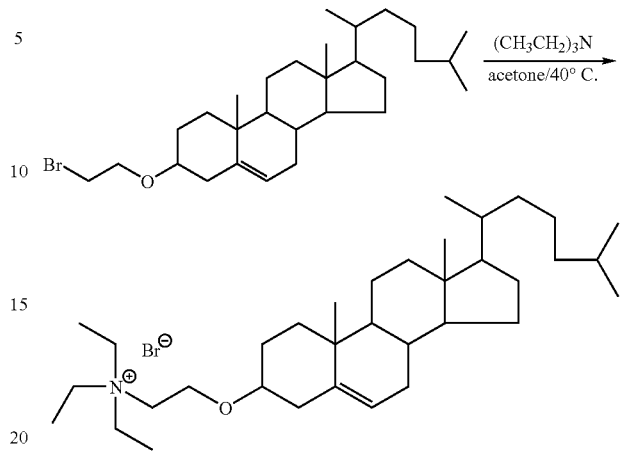

EXAMPLE 5

Synthesis of N-2-[3-(Cholesteryloxy)ethyl]-N,N,N-trimethyl ammonium Bromide 50 ml of purified trimethyl amine was added in the reactor which contained 5 g (0.01 mol) of 3-(2-bromoethyl)cholesterol and 250 ml of anhydrous acetone and the mixture was stirred for 48 hours at 35~40° C. During reaction white solid was formed in acetone solvent and the end of reaction was confirmed by TLC.

The product was purified by silica gel column using chloroform:methanol (7:3) and by recrystallization method using anhydrous ethanol to give 2.1 g of moisture-sensitive white crystal (35.6%).

$^1$H NMR(CDCl$_3$, ppm): 5.3(t, 1H, C of cholesterol=C$\underline{H}$)
3.9(s, 4H, —NC$\underline{H}_2$C$\underline{H}_2$O—)
3.5(s, 9H, (CH$_3$)$_3$N—)

The reaction process of example 5 is illustrated in the following reaction scheme 5.

[REACTION 5]

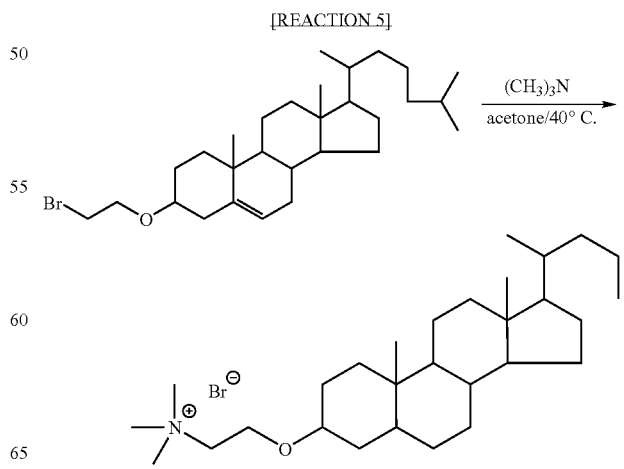

EXAMPLE 6

Synthesis of N-Cholesteryloxyethyl-N,N,N-trihydroxyethyl Ammonium Bromide (CETA)

5 g (10.13 mmol) of 2-bromoethyl cholesteryl ether and 20 ml of triethanolamine were simultaneously added in 50 ml of anhydrous acetone, and the mixture was stirred for 48 hours at 50° C. The crystal product was filtered by glass filter and was dried on vacuum pump. Then, the product was purified by silica gel column using chloroform:methanol (4:1) and by re-crystallization using anhydrous ethanol to give 2 g of white crystal (30%).

$^1$H NMR(CDCl$_3$, ppm): 5.3(t, 1H, C of cholesterol=C$\underline{H}$) 5.0(s, 3H, $\underline{H}$OCH$_2$CH$_2$)
4.2(t, 6H, HOC$\underline{H}_2$CH$_2$N—)
3.5~4.0(m, 8H, (HOCH$_2$C$\underline{H}_2$)$_3$NC$\underline{H}_2$CH$_2$O—)

The reaction process of example 6 is illustrated in the following reaction scheme 6.

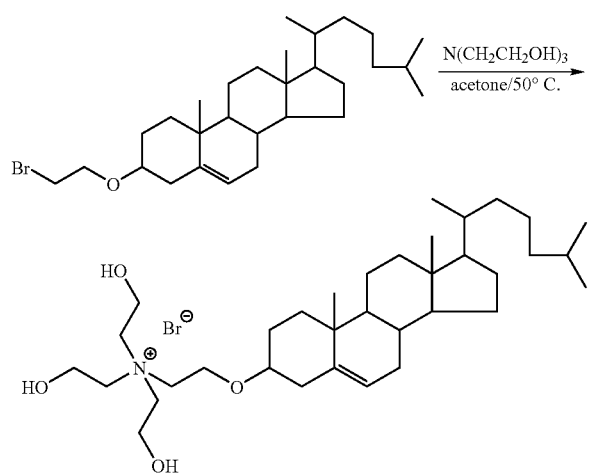

EXAMPLE 7

Preparation of Plasmid DNA

To purification of plasmid DNA, the bacteria strain was used a DH5α strain of E. coli transformed by of pCMV-β-gal plasmid and DH5α E. coli transformed by pCIS-CAT plasmid. E. coli was obtained from the colony cultured in LB-ampicillin solid media and was inoculated to LB broth liquid media containing 20 μl/ml of ampicillin and was cultured at 37° C. for 16 hours.

Figure 1:
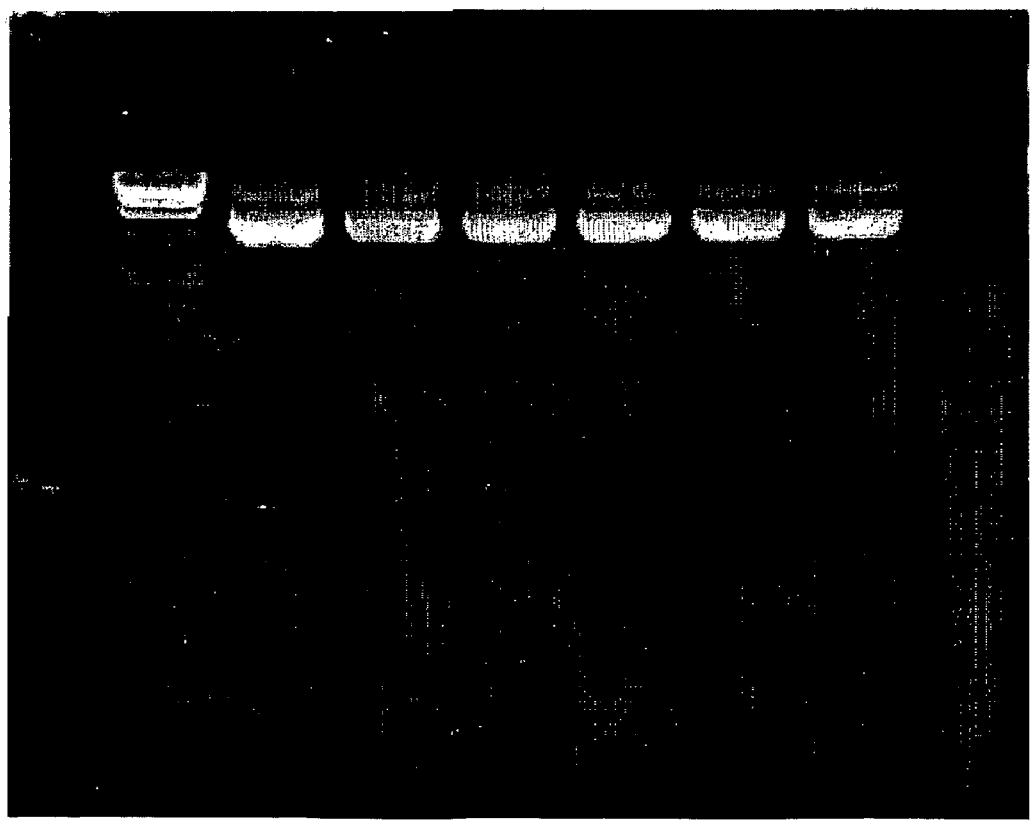
FIG. 1 illustrates electrophoresis finding of naked pCMV-p53 plasmid DNA which is free of contamination by DNA or RNA of E. coli, in which most of the DNAs are composed of supercoiled plasmid DNAs, and number indicates serial number of batch of DNA and M λ Hind III marker, respectively.
Figure 2:
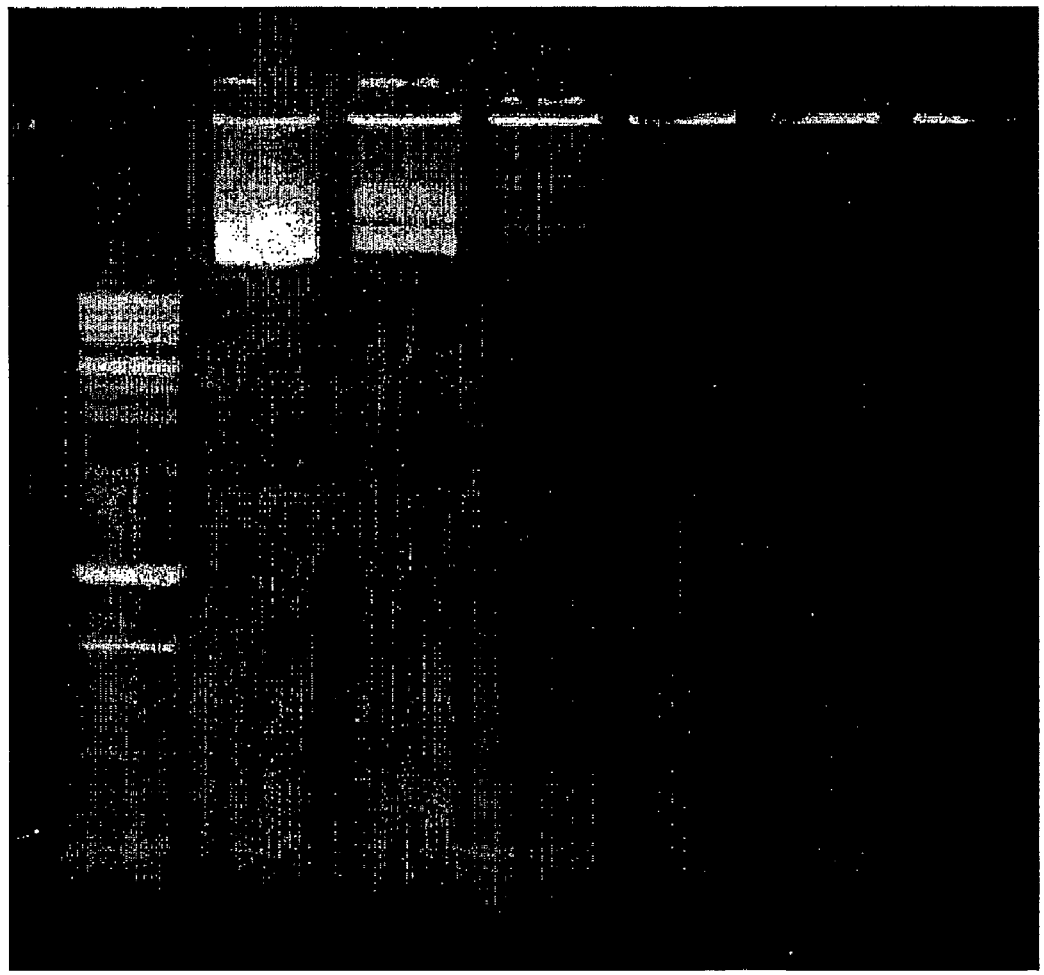
FIG. 2 illustrates electrophoresis (0.8% agarose gel) finding of DNA by which binding efficiency of liposome with pCMV-p53 plasmid DNA was tested.

Plasmid DNA was isolated as follows by using Qiagen plasmid DNA purification kit (Qiagen, Germany). First, the cell mass of E. coli were separated from culture fluid by centrifugation (5,000×g) at 4° C. for 10 minutes, followed by resuspension in 10 ml of P1 buffer solution. This resuspended mixture was incubated at room temperature for 5 min and added by 10 ml of P3 buffer solution and kept for 20 min in ice bath. After centrifugation (30,000×g) at 4° C. for 30 min, supernatants were put into column equilibrized in QBT buffer solution, washed twice with 30 ml of QC buffer solution, eluted by 5 ml of QF buffer solution, and added by 0.7× volume of isopropanol. Then DNA was precipitated by centrifugation (20,000×g) at 4° C. for 30 min. Recovered DNA was washed by 70% ethanol, dried in the air, dissolved in distilled water and their quantity and quality were analyzed by using UV-spectrophotometer. The endotoxin concentration of extracted DNA in the way above was confirmed to be less than 10 endotoxin units/mg DNA on limulus amebocyte lysate (LAL) test. In addition, the recovered DNA was loaded on 1% agarose gel electrophoresis, which showed that most of the recovered plasmid DNA was supercoiled form DNA (See FIG. 1).

EXAMPLE 8

Synthesis of Cationic Liposome

When cationic lipids obtained by the methods of EXAMPLE 1 to 6 are mixed with helper lipid such as DOPE or mPEG-cholesterol, a variety of cationic liposome are formed. In this study the optimal molar ratio of cationic lipids and helper lipid were investigated which can provide the best quality liposome (ie. highest gene transfer efficiency), which were then used for in vitro gene transfer experiment. Synthesis of cationic liposome from the cationic lipid in EXAMPLE 1 is described here in EXAMPLE 8 as a typical model. Cationic liposome was also prepared from cationic lipids of EXAMPLE 2 to 6 in the same method.

A mixture of cationic lipid in EXAMPLE 1 and DOPE and mPEG-cholesterol (1:1:0.2 molar ratio) and another mixture of cationic lipid in EXAMPLE 2 and DOPE (1:1 molar ratio) were prepared respectively and both lipid mixtures were put into 2 ml Wheaton glass septum vial, dissolved in excess chloroform and were made into lipid film by low speed evaporation until nearly all of the chloroform became vaporized in nitrogen environment. Recovered lipid films were dried again for 12 hours in order to completely remove solvent. In order to produce large MLV, lipid films were added by 1 ml of endotoxin-free milliQ water, sealed tightly inside vial at 37° C. and stirred for 1 minute. Small unilamellar vesicle was synthesized by passing the large vesicle through 0.1 μm polycarbonate film for 30-times by using mini-extruder (Avanti Polar Lipids, Inc., USA). Small unilamellar vesicle (SUV) was also produced by using invert cup ultrasonic sonicator (Heat Systems, USA), in which vesicles were treated by supersonic waves for 60 minutes in nitrogen environment. All of the recovered liposome were sterilized by filtration using 0.22 μm filter and were stored at 4° C. until use. The diameters of liposome were measured by light scattering analysis: The mean diameter of liposome ranged from 100 nm to 150 nm.

EXAMPLE 9

Test of Optimal Ratio of DNA and Cationic Liposome

In order to identify the optimal ratio of cationic liposome and plasmid DNA in which liposome and DNA combine with each other completely, liposome were mixed with plasmid DNA in variable ratio and the mixture were loaded on electrophoresis, and mobility of each liposome-DNA mixture was investigated. Cationic lipids of EXAMPLE 1 to 6 were mixed with DOPE in 1:1 molar ratio to make cationic liposome. Cationic liposome were mixed with λ Hind III Marker DNA in weight ratio of 1 to 2, 1 to 1, 2 to 1, 3 to 1, 4 to 1, 5 to 1, 6 to 1, 7 to 1 and 8 to 1, respectively, and all the mixtures were left in room temperature for 15 min. Each mixture of cationic liposome and DNA was carefully loaded on to 0.8% agarose gel and electrophoresis was carried out in 50V. Cationic liposome made of cationic lipid in EXAMPLE 1 to 6 and DOPE showed remarkable DNA binding activity. All of the DNA were found to be completely bound by cationic liposome at ratio of 1 to 4 or more, which means the point when overall charge of cationic liposome:DNA complex begin to form cation. In addition, cationic liposome made of cationic lipid:DOPE:mPEG-cholesterol (1:1:0.2 molar ratio) also showed nearly same results as above.

EXAMPLE 10

Manufacture of Plasmid DNA/Cationic Liposome Complex for Testing In Vitro Gene Transfer Efficiency 0.5 ml of plasmid DNA (mg/ml) and 0.5-4.0 ml of liposome (mg/ml) were slowly mixed and resultant complex were left at room temperature for 15 minutes before applying them to media of cultured cells in vitro. These cationic liposome: plasmid DNA complex carry positive charge because of excess cationic lipids and thus can deliver DNA into cells efficiently and consistently.

EXAMPLE 11

Cell Culture

Each of cell lines of HeLaS3, HepG2, Hep3B, NIH3T3 and COS-7 was purchased from ATCC (American Type Culture Collection, USA) and DMEM media, 10% fetal bovine serum, 100 units/ml penicillin and 100 µg/ml streptomycin from GIBCO BRL (USA), respectively. Cells were cultured for transfection study until 60~80% confluency in 6-well plates (Falcon Ware, Benton Dickinson, USA), when DNA: liposome complex of Example 10 were administered to the cells.

Complex of 1 µg of pCMV-β-gal plasmid and 4 µg of cationic liposome was administered into each well, incubated for 4 hours and then media was changed into regular media not containing transfection reagent. After additional culture for 48 hours (for X-Gal staining) or 24 hours (for CAT or luciferase assay) at 37° C./$CO_2$ incubator, the cells were tested for gene transfer efficiency.

EXAMPLE 12

In Vitro Gene Transfection (Lipofection) Assays

Each of the cell lines was seeded into 6-well plates at density of $1\times10^5$ cells/well on 1 day before transfection. The transfection was carried out when the cells in each well grew about 60~80% confluency. Plasmid DNA and cationic liposome were mixed at ratio of 1 to 4, 1 to 5 or 1 to 6, and the resultant complexes were left at room temperature for 15 min. The media of each well was changed into serum free media alone or serum free media containing DNA:cationic liposome complex. After 4 hours' culture inside 37° C./$CO_2$ incubator, 1 ml of regular media containing serum were added into each well and cells were cultured for additional 24 or 48-hours. The cellular transfection protocol used in this study were as follows:

1) 100 µl of serum free DMEM media is added into two microcentrifuge (Eppendorf) tubes, followed by addition of cationic liposome and DNA in optimal ratio.

2) DNA is slowly added into liposome solution inside micro tube and the mixture are slowly pipetted twice or thrice and left at room temperature for 15 min.

3) After 10 min, media of each well of multiwell culture plates are removed and changed into serum free media 4) 800 µl of serum free media are added into micro tubes which contain 200 µl of DNA/liposome complex solutions.

5) Media in each well are removed.

6) Serum free media only are added into wells of control group.

7) 1 ml of media containing cationic liposome:DNA mixture(of 4) are added into each well of gene transfer group, culture plates are gently rotated to evenly distribute media and cells are observed under inverted microscopy.

8) The culture plates are again placed inside 37° C./$CO_2$ incubator and cultured for 4 hours.

9) One ml of serum containing regular media are added into each well and cells are cultured for additional 24 or 48-hours, after which cellular transfection assay are performed.

EXAMPLE 13

Gene Transfer Efficiency Test by Using X-Gal Staining

Cells in EXAMPLE 12 were washed twice by PBS and were fixed in 0.5% glutaldehyde PBS solution at room temperature for 15 min. Fixative solutions were removed, washed twice by PBS, and incubated with X-gal solution (Stratagene, USA) in 37° C. for 3~5 hours. X-Gal staining solution was prepared by mixing X-gal (Stratagene, USA) in DMSO solution (1 mg/ml X-Gal) and X-Gal buffer solution (0.01% sodium deoxycholates, 0.02% NP-40, 2 mM $MgCl_2$, 5 mM ferrocyanide, 5 mM ferricyanide, 0.01M PBS), followed by filtration using 0.45 µm filter. On X-Gal staining, most of the cell lines tested showed high gene transfer efficiency of cationic liposome made in this invention. In particular, COS 7, Hep 3B and NIH 3T3 cell lines showed high level expression with positive X-Gal staining in more than 25% of total cells.

EXAMPLE 14

Gene Transfer Efficiency Tests by Using CAT Assay

Recovered cells at the end of EXAMPLE 12 are resuspended in 100 µl of 200 mM Tris-HCl buffer solution (pH 7.4) and 50 µl of supernatant were obtained after several freezing/thawing cycles of treatment, and were then added by 40 µl of Tris-HCl solution which contained $^{14}$C-tagged chloramphenicol (0.1µ Cis; specific activity, 47µ Ci/mmols; 1 Ci=37 Gbq), followed 5 min later by addition of 20 µl of 4 mM acetyl CoA at 37° C. After 1 hour's incubation at 37° C., chloramphenicol and acetylated derivatives were extracted by using ethylacetate, separated by using TLC and were analyzed by autoradiograph.

The X ray film was analyzed by using LKB UltroScan densitometer, which showed markedly higher CAT activity in cells administered with complex of cationic liposome and DNA as compared with control cells.

EXAMPLE 15

Electron Microscopic Examination

Samples were suspended in water using ultrasonic waves disperser to make lipid vesicles. Lipid vesicle solution were mixed with 2% uranyl acetate in 1:1 volume ratio. 0.02 ml of lipid vesicle solution and equal volume of 2% uranyl acetate solution were dropped on to microscopic slide and were mixed well. Small volume of lipid vesicle:uranyl acetate complex solution are dropped on the top of grid which are coated by formvar membrane, dried for 3 hours and then were observed under electron microscopy. If it is dried less than 3 hours, the formvar membrane might be broken upon scanning electron beam on electron microscopy. 24 hours of drying at room temperature is optimal. Scanning electron microscopic findings showed vesicle with globular shape multilamellar structure and average diameter of 100-150 nm (FIG. 3).

INDUSTRIAL APPLICABILITY

Cationic lipids in this invention carry multiple cationic charges, can deliver gene or other biologically active molecules inside cells efficiently, are devoid of significant cellular toxicity and chemically stable, and therefore are ideal gene and drug delivery vehicles for the gene therapy or anticancer therapy in clinical practice. In addition, their synthesis, purification and quality control are easy and they cost just a little money and therefore also have high economical efficiency.

The invention claimed is:

1. Cationic lipids represented by the following chemical structure 1:

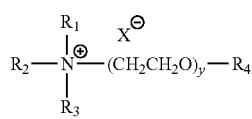

[Chemical structure 1]

wherein Y is natural number between 1 and 20; each of $R_1 \sim R_3$ has same or different hydrogen, alkyl or hydroxyalkyl radical between 1~10 of carbon number, or aryl or aralkyl radical between 7~11 of carbon number; $R_4$ is cholesterol radical; and X is any anion which is pharmacologically allowable.

2. Cationic lipids according to claim 1, wherein X is Br, Cl, I, $CH_3CO_2$ or $CF_3CO_2$.

3. A process for preparing cationic lipids represented by the following chemical structure 1, comprising;
   (a) a step for mixing cholesterol, pyridine, and methanesulfonyl chloride to prepare cholesteryl mesylate;
   (b) a step for mixing said cholesteryl mesylate and 2-bromoethanol in acetonitrile to obtain 2-bromoethoxycholesterol; and
   (c) a step for mixing said 2-bromoethoxycholesterol and N,N-dimethylethanolamine in acetone to prepare N-cholesteryloxyethyl-N,N-dimethyl-N-hydroxyethyl ammonium bromide:

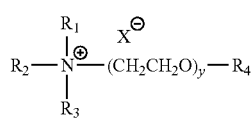

[Chemical structure 1]

wherein Y is 1; each of $R_1$ and $R_3$ is methyl; $R_2$ is hydroxyethyl; $R_4$ is cholesterol radical; and X is bromine.

4. A process for preparing cationic lipids represented by the following chemical structure 1, comprising;
   (a) a step for mixing cholesterol, pyridine, and methanesulfonyl chloride to prepare cholesteryl mesylate;
   (b) a step for mixing said cholesteryl mesylate and 2-bromoethanol in acetonitrile to obtain 2-bromoethoxycholesterol; and
   (c) a step for mixing said 2-bromoethoxycholesterol with one selected from the group consisting of N,N-dimethylamino-2-propanol, triethylamine, trimethylamine and triethanolamine:

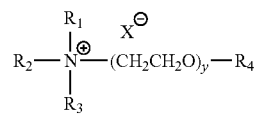

[Chemical structure 1]

wherein Y is 1; each of $R_1 \sim R_3$ has same or different hydrogen, alkyl or hydroxyalkyl radical between 1~10 of carbon number; $R_4$ is cholesterol radical; and X is bromine.

5. A method for delivering anionic molecules into target cells, comprising;
   (a) a step for forming a lipid complex by contacting effective amounts of cationic lipids according to claim 1 and anionic molecules; and
   (b) a step for contacting the lipid complex in step (a) and target cells.

6. The method for delivering anionic molecules into target cells according to claim 5, wherein the lipid complex contains one or more additional lipids.

7. The method for delivering anionic molecules into target cells according to claim 5, wherein additional lipids are at least one selected from the group consisting of DOPE, DOPC, PC, mPEG-cholesterol and cholesterol.

8. The method for delivering anionic molecules into target cells according to claim 5, wherein anionic molecules are DNA, RNA, protein, peptide or biologically active drugs.

9. The method for delivering anionic molecules into target cells according to claim 5, wherein target cells are mammalian cells including HeLaS3, HepG2, Hep3B, NIH 3T3 or COS7.

10. A process for preparing cationic lipids represented by the following chemical structure 1, comprising;
    (a) a step for mixing cholesterol, pyridine, and methanesulfonyl chloride to prepare cholesteryl mesylate;
    (b) a step for mixing said cholesteryl mesylate and triethyleneglycol in acetonitrile and 1,4-dioxane to obtain cholesteryl triethyleneglycol;
    (c) a step for mixing said cholesteryl triethyleneglycol, methanesulfonylchioride and pyridine to prepare cholesteryl triethyleneglycol mesylate;
    (d) a step for mixing said cholesteryl triethyleneglycol mesylate with toluene, potassium butoxide and dimethylethanolamine to obtain 3-(N,N-dimethylaminotetraethoxy)cholesterol; and
    (e) a step for reacting said 3-(N,N-dimethylaminotetraethoxy)cholesterol in acetonitrile under high pressure to prepare N-(tetraethoxycholesteryl)-N,N,N-trimethyl ammonium chloride:

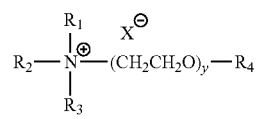

[Chemical structure 1]

wherein Y is 4; each of $R_1 \sim R_3$ is methyl; $R_4$ is cholesterol radical; and X is chloride.

* * * * *